United States Patent
Feather et al.

(10) Patent No.: US 11,483,545 B2
(45) Date of Patent: Oct. 25, 2022

(54) DYNAMIC ILLUMINATION FOR EYE-TRACKING

(71) Applicant: Intuitive Surgical Operations, Inc., Sunnyvale, CA (US)

(72) Inventors: Heath Feather, Cupertino, CA (US); Randal P. Goldberg, San Mateo, CA (US); Alexandre V. Matveev, Santa Clara, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 17/271,522

(22) PCT Filed: Aug. 28, 2019

(86) PCT No.: PCT/US2019/048628
§ 371 (c)(1),
(2) Date: Feb. 25, 2021

(87) PCT Pub. No.: WO2020/047140
PCT Pub. Date: Mar. 5, 2020

(65) Prior Publication Data
US 2021/0344896 A1    Nov. 4, 2021

Related U.S. Application Data

(60) Provisional application No. 62/724,346, filed on Aug. 29, 2018.

(51) Int. Cl.
*H04N 13/383* (2018.01)
*G02B 30/35* (2020.01)
(Continued)

(52) U.S. Cl.
CPC ............ *H04N 13/383* (2018.05); *G02B 1/11* (2013.01); *G02B 27/0093* (2013.01); *G02B 30/35* (2020.01); *H04N 5/2256* (2013.01)

(58) Field of Classification Search
CPC ........... G02B 27/0093; G02B 27/0172; G02B 30/35; G02B 1/11; G02B 2027/0134;
(Continued)

(56) References Cited

U.S. PATENT DOCUMENTS

| 2003/0095081 A1* | 5/2003 | Furness, III ............ G09G 3/02 345/32 |
| 2005/0053274 A1* | 3/2005 | Mayer ................. H04N 13/239 348/E13.016 |

(Continued)

OTHER PUBLICATIONS

International Search Report and Written Opinion for Application No. PCT/US2019/048628, dated Nov. 15, 2019, 14 pages.
(Continued)

*Primary Examiner* — Neil R Mikeska (57) ABSTRACT

An apparatus includes a controller coupled to a stereoscopic image viewer. The stereoscopic image viewer includes a viewing lens, an image capture unit, and a plurality of light sources. The image capture unit is configured to capture image frames. The controller receives the captured image frames. The controller is configured to switch light output from one of the plurality of light sources to another one of the plurality of light sources if a corneal reflection in a captured image frame intersects a fixed reflection in the captured image frame.

8 Claims, 7 Drawing Sheets

(51) Int. Cl.
   *G02B 1/11*    (2015.01)
   *G02B 27/00*   (2006.01)
   *H04N 5/225*   (2006.01)
(58) Field of Classification Search
   CPC .. H04N 5/2256; H04N 13/344; H04N 13/383;
                              G06V 40/18; A61B 3/113
   See application file for complete search history.

(56) References Cited

U.S. PATENT DOCUMENTS

| | | |
|---|---|---|
| 2015/0160725 A1 | 6/2015 | Lee et al. |
| 2015/0310253 A1 | 10/2015 | Agrawal et al. |
| 2016/0225153 A1* | 8/2016 | Kim .......................... G06T 7/64 |
| 2016/0270655 A1 | 9/2016 | Caraffi et al. |
| 2017/0031435 A1 | 2/2017 | Raffle et al. |
| 2017/0316264 A1 | 11/2017 | Gustafsson et al. |
| 2018/0232048 A1* | 8/2018 | Popovich ............... A61B 3/113 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Preliminary Report on Patentability for Application No. PCT/US2019/048628, dated Mar. 11, 2021, 8 pages.

* cited by examiner

DYNAMIC ILLUMINATION FOR EYE-TRACKING

RELATED APPLICATIONS

The present application is a U.S. National Stage Application under 35 U.S.C. § 371 of International Application No. PCT/US2019/048628, filed on Aug. 28, 2019, which claims priority to U.S. Provisional Patent Application No. 62/724,346, filed on Aug. 29, 2018, the contents of which are hereby incorporated by reference in their entirety.

BACKGROUND

Field of the Invention

The present invention relates generally to stereoscopic image viewers, and more particularly to processing fixed reflections during eye-tracking through a stereoscopic image viewer.

Description of Related Art

Figure 1:
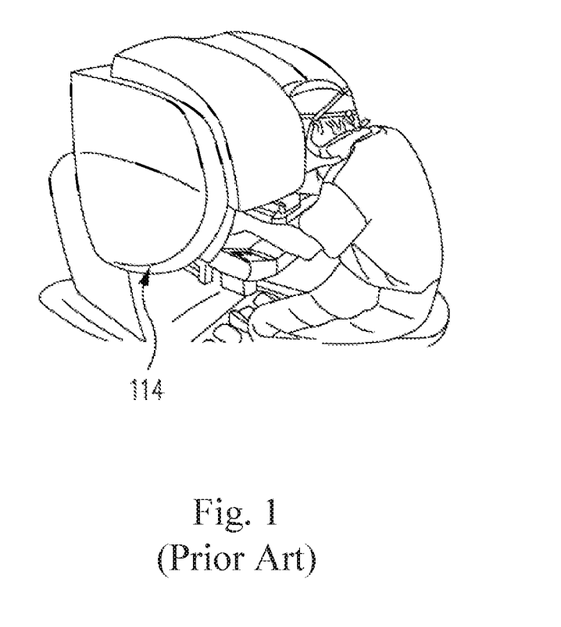
FIG. 1 is an illustration of a surgeon's console from a prior art teleoperated computer-assisted medical system.

A surgeon's console 114 (FIG. 1) is commonly part of a teleoperated computer-assisted medical system. A user sitting at surgeon's console 114 looks through lenses mounted in surgeon's console 114 to view a stereoscopic image of a site of interest. Surgeon's console 114 includes a user manipulated mechanical mechanism that allows a user to adjust a spacing between the lenses of the stereoscopic image viewer to match the user's interpupillary distance.

Similarly, a head mounted display device includes lens used to view a stereoscopic image. Various mechanisms have been developed to facilitate viewing a stereoscopic image. See, for example, U.S. Pat. No. 9,600,068 B2 (issued on Mar. 21, 2017, disclosing "Digital Inter-Pupillary Distance Adjustment") and U.S. Patent Application Publication No. US 2017/0344107 A1 (filed on May 25, 2016, disclosing "Automatic View Adjustments for Computing Devices Based on Interpupillary Distances Associated with their Users").

SUMMARY

In one aspect, an apparatus includes a stereoscopic image viewer that is configured to track the gaze of a user via eye-tracking. Specifically, images of the user's irises/pupils and corneal reflections captured by an image capture unit in the stereoscopic image viewer are used to determine a direction of the user's gaze. A corneal reflection is commonly referred to as a glint.

The structure of the stereoscopic image viewer also creates one of more fixed reflections that are captured along with the images of the user's irises/pupils and the corneal reflections. The location of a fixed reflection does not change from captured frame to captured frame so long as a location of light illuminating the user's eyes in the stereoscopic image viewer does not change.

If a corneal reflection were to intersect with a fixed reflection, the accuracy of tracking the user's gaze would be degraded. Hence in one aspect, if a corneal reflection intersects a fixed reflection, a controller, coupled to the stereoscopic image viewer, causes the fixed reflection to be moved to a different location so that the corneal reflection no longer intersects with the fixed reflection. Thus, eye-tracking can be used in the presence of fixed reflections without concern that the fixed reflection will interfere with the eye-tracking.

In one aspect, an apparatus includes a stereoscopic image viewer and a controller. The stereoscopic image viewer includes a viewing lens, an image capture unit, and a plurality of light sources. The viewing lens includes a plurality of components. The image capture unit is configured to capture image frames. The plurality of light sources is configured to pass light through the viewing lens. The controller is coupled to the stereoscopic image viewer to receive captured image frames and is coupled to the plurality of light sources. The controller is configured to control light output from each of the plurality of light sources, and is configured to switch light output from one of the plurality of light sources to another one of the plurality of light sources if a corneal reflection in a captured image frame intersects a fixed reflection in that captured image frame.

In this aspect, the viewing lens includes an outer surface, and an anti-reflective coating for light from the plurality of light sources. The anti-reflective coating is on the outer surface of the viewing lens. In another aspect, an outer perimeter of each of a plurality of lens used in making the viewing lens is coated with an anti-reflective coating.

In one aspect, the plurality of light sources is a plurality of non-visible light sources. In another aspect, the plurality of non-visible light sources is a plurality of infrared light sources.

In one aspect, the image capture unit includes a lens assembly, and the plurality of light sources includes a first light source displaced in a first direction from the lens assembly of the image capture unit; and a second first light source displaced in a second direction from the lens assembly of the image capture unit. The first direction is opposite to the second direction. In still another aspect, one or more of the plurality of light sources includes more than one light source.

In another aspect, an apparatus includes a stereoscopic image viewer and a controller. The controller is coupled to the stereoscopic image viewer to receive image frames captured within the stereoscopic image viewer and to control an eye-tracking illuminator included within the stereoscopic image viewer.

In this aspect, the stereoscopic image viewer includes a first lens, a second lens, an image capture unit, and the eye-tracking illuminator. The image capture unit is configured to capture image frames. In one aspect, a captured image frame includes (i) a right eye image captured from first light reflected from a right eye of a user and (ii) a left eye image captured from second light reflected from a left eye of the user. The first reflected light passes through the first lens of the stereoscopic image viewer before being captured by the image capture unit. Similarly, the second reflected light passing through the second lens before being captured by the image capture unit. The eye-tracking illuminator includes a plurality of light sources configured to illuminate the left and right eyes with light after the light passes through the first and second lenses. In one aspect, the light is non-visible light.

The controller is configured to control light output from each of the plurality of light sources, and is configured to stop light output from one of the plurality of light sources if the light output from the one of the plurality of light sources results in intersection of a glint and a fixed reflection in a captured image frame. The glint is used in tracking of a gaze of the user.

In this apparatus, the stereoscopic image viewer also includes a first movable viewing assembly and a second movable viewing assembly. The first and second movable viewing assemblies are contained within a housing of the stereoscopic image viewer.

The first movable viewing assembly includes the first lens and a first reflective structure. The first reflective structure reflects first visible light, passes a first portion of the light from the plurality of light sources, and passes reflected light from the first portion of the light from the plurality of light sources. The first reflective structure is positioned to reflect the first visible light into the first lens, to pass the first portion of the light from the plurality of light sources toward the first lens, and to pass reflected light from the first portion of the light from the plurality of light sources toward the image capture unit.

The second movable viewing assembly includes the second lens and a second reflective structure. The second reflective structure reflects second visible light, passes a second portion of the light from the plurality of light sources and passes reflected light from the second portion of the light from the plurality of light sources. The second reflective structure is positioned to reflect the second visible light into the second lens, to pass the second portion of the light from the plurality of light sources toward the second lens, and to pass reflected light from the second portion of the light from the plurality of light sources toward the image capture unit.

In one aspect, the first lens is fixedly coupled to the first reflective structure in the first movable viewing assembly so that the first lens and the first reflective structure move as a unit as the first movable viewing assembly moves. Similarly, the second lens is fixedly coupled to the second reflective structure in the second movable viewing assembly so that the second lens and the second reflective structure move as a unit as the second movable viewing assembly moves.

The first movable viewing assembly also includes a first display unit mounted in the first movable viewing assembly to provide the first visible light to the first reflective structure. The first display unit is fixedly coupled to the first reflective structure in the first movable viewing assembly so that the first lens, the first reflective structure, and the first display unit move as a unit as the first movable viewing assembly moves. Similarly, the second movable viewing assembly includes a second display unit mounted in the second movable viewing assembly to provide the second visible light to the second reflective structure. The second display unit is fixedly coupled to the second reflective structure in the second movable viewing assembly so that the second lens, the second reflective structure, and the second display unit move as a unit as the second movable viewing assembly moves.

In one aspect, the first reflective structure includes a dichroic surface. In this aspect, the second reflective structure also includes a dichroic surface. In another aspect, the first reflective structure includes a ninety percent reflective surface, and the second reflective structure also includes a ninety percent reflective surface.

Each of the first lens and the second lens includes a plurality of lens combined to together to form a single lens structure. The single lens structure includes an outer surface and an anti-reflective coating for light from the plurality of light sources. The anti-reflective coating coats the outer surface of the single lens structure. In another aspect, the single lens structure includes a plurality of lenses and an outer perimeter of each of the plurality of lenses is coated with the anti-reflective coating.

In another aspect, the controller is configured to cause a different one of the plurality of light sources to output light if the light output from the one of the plurality of light sources is stopped. The plurality of light sources includes a first set of light sources and a second set of light sources. The first set of light sources is configured to illuminate a first eye of a user with light after the light passes through the first lens. The second set of light source is configured to illuminate a second eye of the user with light after the light passes through the second lens. The controller is configured to control light output from each of the plurality of light sources. The controller is configured to individually command each one of the first set of light sources to output light and to stop the output of the light. Similarly, the controller is configured to individually command each one of the second set of light sources to output light and to stop the output of the light.

In one aspect, the plurality of light sources is a plurality of non-visible light sources. In still another aspect, the plurality of non-visible light sources is a plurality of infrared light sources.

In still a further aspect, a medical system includes a controller coupled to a stereoscopic image viewer to receive captured image frames from an image capture unit of the stereoscopic image viewer and coupled to a plurality of light sources of the stereoscopic image viewer. Each of the plurality of light sources is configured to pass light through a lens of the stereoscopic image viewer to illuminate at least a portion of a human eye. The image capture unit is positioned to receive reflected light passed through the lens to the image capture unit.

The controller is configured to individually control light output from each of a plurality of light sources. Specifically, the controller is configured to stop light output from any one of the plurality of light sources if the light output from that one of the plurality of light sources results in an intersection of a glint and a fixed reflection in a captured image frame. The glint is used to track a gaze of a user.

The controller also is configured to cause a different one of the of the plurality of light sources to output light if the light output from the one of the plurality of light sources is stopped. The controller is configured to command the one of the plurality of light sources to output light.

A method includes stopping, by a controller, light output from one of the plurality of light sources within a stereoscopic image viewer if the light output from the one of the plurality of light sources results in an intersection of a glint and a fixed reflection in a captured image frame. The glint is used to track a gaze of a user. The captured image frame is captured by an image capture unit within the stereoscopic image viewer.

This method also includes the controller commanding a different one of the plurality of light sources to output light if the light output from the one of the plurality of light sources is stopped. The method, in addition, includes commanding, by the controller, the one of the plurality of light sources to output light prior to the stopping.

In another aspect, a method includes generating, by a controller, a first bitmap representing reflections in a first image frame captured by an image capture unit within a stereoscopic image viewer, and generating, by the controller, a second bitmap representing reflections in a second image frame captured by the image capture unit within the stereoscopic image viewer. The controller subtracts the second bitmap from the first bitmap to obtain a new bitmap. The controller stops light output from one of a plurality of light sources within the stereoscopic image viewer if all bits in the new bitmap have a same state. In one aspect, the controller commands a different one of the plurality of light sources to output light if the light output from the one of the plurality of light sources is stopped.

BRIEF DESCRIPTION OF THE DRAWINGS

In the drawings, for single digit figure numbers, the first digit in the reference numeral of an element is the number of the figure in which that element first appears.

DETAILED DESCRIPTION

A stereoscopic image viewer 200 (FIG. 2A) includes a single eye-tracking image capture unit 210, e.g., a camera, mounted within stereoscopic image viewer 200. Eye-tracking image capture unit 210 captures a frame that includes an image of each of a user's eyes 290-L, 290-R. The captured imaged may also include a reflections from the user's corneas and fixed reflections. Fixed reflections are caused by features of stereoscopic image viewer 200. So long as a spacing between viewing lenses in stereoscopic image viewer 200 does not change, the locations of fixed reflections caused by the features of stereoscopic image viewer 200 do not change from captured frame to captured frame. However, corneal reflections change locations from captured frame to captured frame as the user's gaze changes from captured frame to captured frame. Herein, a corneal reflection is sometimes referred to as a glint.

Figure 2A:
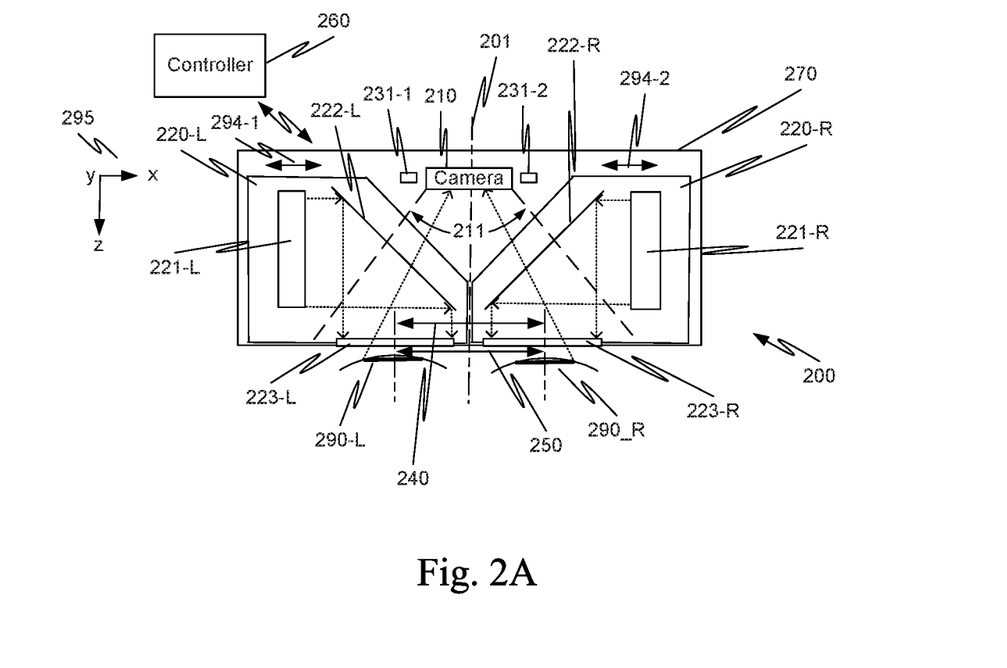
FIG. 2A is an illustration of an apparatus that includes a stereoscopic image viewer and a controller.

A controller 260 coupled to stereoscopic image viewer 200 receives the captured frames. Controller 260 uses information in the captured frames including a corneal reflection to track the gaze of the user. Tracking the gaze of a user is referred to as eye-tracking. If a corneal reflection merges with or is too close to a fixed reflection in a capture image, the accuracy of the eye-tracking can be compromised.

Thus, controller 260 determines for each eye whether the corneal reflection for that eye intersects a fixed reflection. If the corneal reflection intersects a fixed reflection, controller 260 moves the location of the fixed reflection in subsequently captured frames. This prevents the fixed reflection from interfering with accuracy of the eye-tracking.

For example, to move the fixed reflection, controller 260 stops light output from a first illumination source that produces the fixed reflection and initiates light output from a second illumination source to illuminate the user's eye. Switching from the first illumination source to the second illumination source for illumination of the user's eye causes the location of the fixed reflection to change in a subsequently captured frame. Consequently, the corneal reflection no longer intersects the fixed reflection and the fixed reflection does not affect the eye-tracking.

In this aspect, controller 260 controls the location of the fixed reflections in captured frames by controlling light from a plurality of light sources. When light from any one of the plurality of light sources results in a fixed reflection that may interfere with tracking of a user's gaze, controller 260 switches from that light source to another light source in the plurality of light sources to provide illumination for glint formation that is used in eye-tracking.

Herein, a single controller 260 is referenced and described. Although described as a single controller, it is to be appreciated that this controller may be implemented in practice by any one of or any combination of hardware, software that is executed on a processor, and firmware. Also, a controller's functions, as described herein, may be performed by one unit or divided up among different components, each of which may be implemented in turn by any one of or any combination of hardware, software that is executed on a processor, and firmware. When divided up among different components, the components may be centralized in one location or distributed across a computer-aided medical system for distributed processing purposes.

A processor should be understood to include at least a logic unit and a memory associated with the logic unit. Thus, in various embodiments, controller 260 includes programmed instructions (e.g., a non-transitory machine-readable medium storing the instructions) to implement some or all of the methods described in accordance with aspects disclosed herein. Any of a wide variety of centralized or distributed data processing architectures may be employed. Similarly, the programmed instructions may be implemented as a number of separate programs or subroutines, or they may be integrated into a number of other aspects of the systems described herein.

Controller 260 can be coupled to stereoscopic image viewer 200 by a wired connection, a wireless connection, an optical connection, etc. In some embodiments, controller 260 supports wireless communication protocols such as Bluetooth, Infrared Data Association (IrDA) protocol, Home Radio Frequency (HomeRF) protocol, IEEE 802.11 protocol, Digital Enhanced Cordless Telecommunications (DECT) protocol, and Wireless Telemetry protocol.

Eye-tracking image capture unit 210 is mounted within a housing 270 of stereoscopic image viewer 200, i.e., is contained within housing 270. The viewing optics of stereoscopic image viewer 200, i.e., lens assemblies 223-L, 223-R, are mounted in stereoscopic image viewer 200 so that the viewing optics are between a user of stereoscopic image viewer 200 and a lens assembly of eye-tracking image capture unit 210. Thus, with reference to eyes 290-L, 290-R of a user of stereoscopic image viewer 200, eye-tracking image capture unit 210 is mounted behind the viewing optics.

For ease of discussion, a Cartesian x-y-z coordinate system 295 is defined with respect to stereoscopic image viewer 200. Note, FIG. 2A is a top view of stereoscopic image viewer 200. In this top view, a z-axis (a third axis) extends in the up and down directions in FIG. 2A. A y-axis (a second axis) extends into and out of the page while an x-axis (a first axis) extends in the left and right directions (first and second directions).

The location of eye-tracking image capture unit 210 relative to the viewing optics within housing 270 is not critical so long as a field of view 211 of eye-tracking image capture unit 210 includes first lens assembly 223-L and second lens assembly 223-R. This assures that first light reflected from eye 290-L (represented by dotted line between eye 290-L and eye-tracking image capture unit 210) and second light reflected from eye 290-R (represented by dotted line between eye 290-R and eye-tracking image capture unit 210) can be captured in a single frame by eye-tracking image capture unit 210. In this example, the lens of eye-tracking image capture unit 210 is centered on an axis 201 that extends in the z-direction of stereoscopic image viewer 200.

Although FIG. 2A shows a single eye-tracking image capture unit 210, it is understood that in certain examples a plurality of eye-tracking image capture units may be provided within housing 270. For example, a first eye-tracking image capture unit may be configured to capture reflected light from eye 290-L and a second eye-tracking image capture unit may be configured to capture reflected light from eye 290-R. In such examples, the first eye-tracking image capture unit may be configured to only capture reflected light from eye 290-L and the second eye-tracking image capture unit may be configured to only capture reflected light from eye 290-R.

This may be accomplished in any suitable manner. For example, there may be a partition within housing 270 that prevents the first eye-tracking image capture unit from capturing reflected light from eye 290-R and that prevents the second eye-tracking image capture unit from capturing reflected light from eye 290-L.

In addition to eye-tracking image capture unit 210, stereoscopic image viewer 200 also includes a first movable viewing assembly 220-L and a second movable viewing assembly 220-R. In this aspect, second movable viewing assembly 220-R is a mirror image of first movable viewing assembly 220-L about axis 201.

First movable viewing assembly 220-L includes a first display device 221-L, a first reflective structure 222-L, and a first lens assembly 223-L. First display device 221-L, first reflective structure 222-L, and first lens assembly 223-L are mounted in a fixed spatial relationship to each other in first viewing assembly 220-L. Thus, translating first movable viewing assembly 220-L in first and second directions 294-1 along the x-axis moves not only first lens assembly 223-L in the first and second directions 294-1, but also first display device 221-L and first reflective structure 222-L. Consequently, the fixed spatial relationship between first display device 221-L, first reflective structure 222-L and first lens assembly 223-L assures that a first visible light image output by first display device 221-L is reflected by first reflective structure 222-L to first lens assembly 223-L irrespective of the position of first lens assembly 223-L along the x-axis.

Second movable viewing assembly 220-R includes a second display device 221-R, a second reflective structure 222-R, and a second lens assembly 223-R. Second display device 221-R, second reflective structure 222-R, and second lens assembly 223-R are mounted in a fixed spatial relationship to each other in second viewing assembly 220-R. Thus, translating second viewing assembly 220-R in first and second directions 294-2 along the x-axis moves not only second lens assembly 223-R in the first and second directions 294-2, but also second display device 221-R and second reflective structure 222-R. Consequently, the fixed spatial relationship between second display device 221-R, second reflective structure 222-R and second lens assembly 223-R assures that a second visible light image output by second display device 221-R is reflected by second reflective structure 222-R to second lens assembly 223-R irrespective of the position of second lens assembly 223-R along the x-axis.

In one aspect, the first visible light image output from first display device 221-L and the second visible light image output from second display device 221-R are left and right scenes, respectively, captured by an endoscope or other medical instrument when stereoscopic image viewer 200 is part of a computer-assisted medical system, e.g., mounted in surgeon's console 114. Typically, the first and second visible light images are color images, but also could be monochrome, black and white, or gray-scale images.

In one aspect, each of first and second lens assemblies 223-L and 223-R includes a viewing lens and a lens retainer ring. (See FIG. 3.) The lens retainer ring holds the viewing lens in the viewing assembly. In one aspect of the viewing lenses, each viewing lens is made up of plurality of individual lens, e.g., three lenses, four lenses, etc., that are glued together to form the viewing lens.

The characteristics of reflective structures 222-L and 222-R are selected based on the characteristics of the reflected light from an eye of a user, which is captured by eye-tracking image capture unit 210. If the reflected light is visible light, reflective structures 222-L and 222-R are, for example, one-way mirrors. If the reflected light is non-visible light, e.g., infrared light, reflective structures 222-L and 222-R are, in one aspect, dichroic structures that reflect some visible light and pass non-visible light. In yet another aspect, each of reflective structures 222-L and 222-R is a ninety percent reflective mirror on black glass. A ninety percent reflective mirror is a surface that reflects ninety percent of the incident light and passes ten percent of the incident light. Thus, in this aspect, image capture unit 210 sees ten percent of the light reflected from first and second lens assemblies 223-L and 223-R and ten percent of the light reflected from a user's eyes.

Stereoscopic image viewer 200 includes an illuminator that illuminates a user's eyes so that eye-tracking image capture unit 210 can capture frames that are used by controller 260 in eye-tracking. If non-visible light is captured by eye-tracking image capture unit 210, the illuminator includes a plurality of non-visible light sources 231-1 and 231-2 that are mounted adjacent to eye-tracking image capture unit 210. In one aspect, the non-visible light sources are infrared light sources, and a light filter is used on eye-tracking image capture unit 210 to block capture of light that is outside the non-visible spectrum of interest. For example, if the light sources are 880 nanometer light emitting diodes, the filter on the lens of eye-tracking image capture unit 210 blocks light with wavelengths shorter than 830 nanometers.

Although the exemplary illuminator depicted in FIG. 2A shows non-visible light sources 231-1 and 231-2 as being provided adjacent to eye-tracking image capture unit 210, it is understood that an illuminator that illuminates the user's eyes may have different configurations in other implementations. For example, in certain implementations, an illuminator that illuminates the user's eyes may not include non-visible light sources provided adjacent to eye-tracking image capture unit 210. Rather, non-visible light sources may only be provided on a user side of lens assemblies 223-L and 223-R. To illustrate, instead of providing non-visible light sources 231-1 and 231-2 adjacent to eye-tracking image capture unit 210 as shown in FIG. 2A, a non-visible light source (not shown) may be provided partially between first lens assembly 223-L and eye 290-L and an additional non-visible light source (not shown) may be provided partially between second lens assembly 223-R and eye 290-R. Such non-visible light sources may be provided at a periphery of the respective lens assemblies and eyes of the user so as to not inhibit eye tracking. In such examples, the non-visible light source and the additional non-visible light source are configured to both generate a corneal reflection as well as illuminate eyes 290-L and 290-R of the user. In so doing, it may be possible avoid generating fixed reflections such that the only reflections captured by eye-tracking image capture unit 210 are the corneal reflections resulting from non-visible light emitted from the non-visible light source and the additional non-visible light source reflecting off the respective corneas of eyes 290-L and 290-R.

In certain alternative examples, additional non-visible light sources may be provided in addition to the non-visible light sources provided adjacent to eye-tracking image capture unit 210. For example, in addition to non-visible light sources 231-1 and 231-2, a third non-visible light source (not shown) may be provided on a user side of first lens assembly 223-L and a fourth non-visible light source (not shown) may be provided on a user side of second lens assembly 223-R. In such examples, the third and fourth non-visible light sources may be configured to illuminate eyes 290-L and 290-R of the user with additional non-visible light and non-visible light sources 231-1 and 231-2 may be configured to generate the corneal reflections. With such a configuration, a relatively less powerful non-visible light source may be used for non-visible light sources 231-1 and 231-2 because it is not necessary for non-visible light sources 231-1 and 231-2 to both illuminate eyes 290-L and 290-R of the user as well as generate corneal reflections. This in turn results in beneficially minimizing the fixed reflections that may be generated based on the non-visible light emitted from non-visible light sources 231-1 and 231-2 adjacent to eye-tracking image capture unit 210 reflecting from the lens assembly or some other component.

Figure 3:
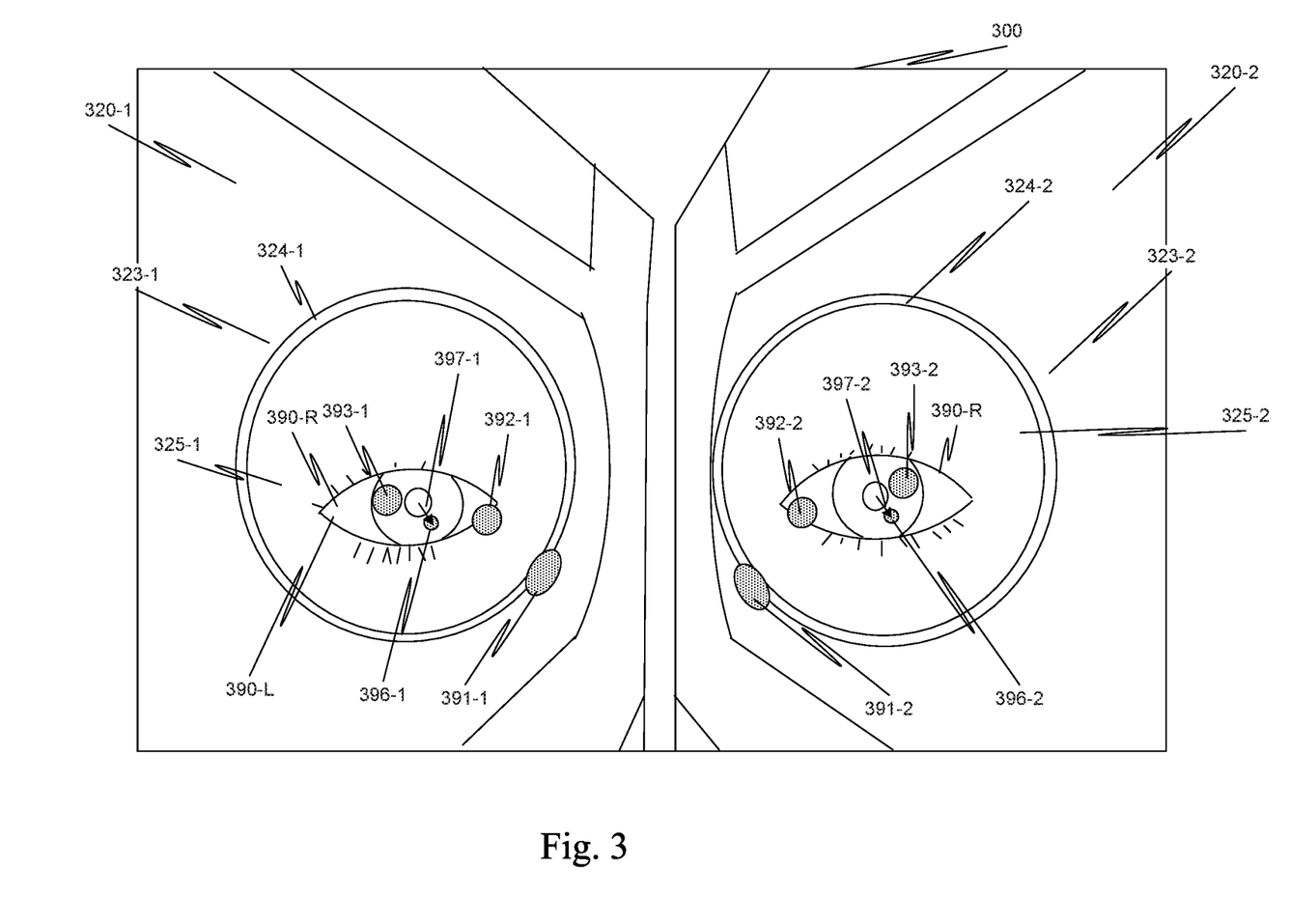
FIG. 3 is a representation of information in a frame captured by an eye-tracking image capture unit of the stereoscopic image viewer of FIG. 2A.

FIG. 3 is a representation of a scene in a frame 300 captured by eye-tracking image capture unit 210. The scene includes an image 320-1 of a portion of first movable viewing assembly 220-L and an image 320-2 of a portion of second movable viewing assembly 220-R. Image 320-1 includes an image 323-1 of first lens assembly 223-L. Image 323-1 includes an image 324-1 of a first lens retainer ring and an image 325-1 of a first lens. Similarly, image 320-2 includes an image 323-2 of second lens assembly 223-R. Image 323-2 includes an image 324-2 of a second lens retainer ring and an image 325-2 of a second lens.

In one aspect, the components of stereoscopic image viewer 200 shown in frame 300, with the exception of the lens retainer rings, in this example, are coated with an anti-reflective coating to minimize stray reflected light that is captured by eye-tracking image capture unit 210. In another aspect, the outer perimeter of each viewing lens is coated with an anti-reflective coating, and in still yet another aspect, the outer perimeter of each lens making up the viewing lens is coated with an anti-reflective coating.

An image 390-L of the user's left eye 290-L and an image 390-R of the user's right eye 290L are also captured in frame 300. Each image of the eye includes an image of the iris and an image of the pupil. Other features of the user's face in the vicinity of the eyes are typically also captured in frame 300, but these are not shown in FIG. 3, because the other features are not needed to understand the novel aspects described herein.

Figure 2B:
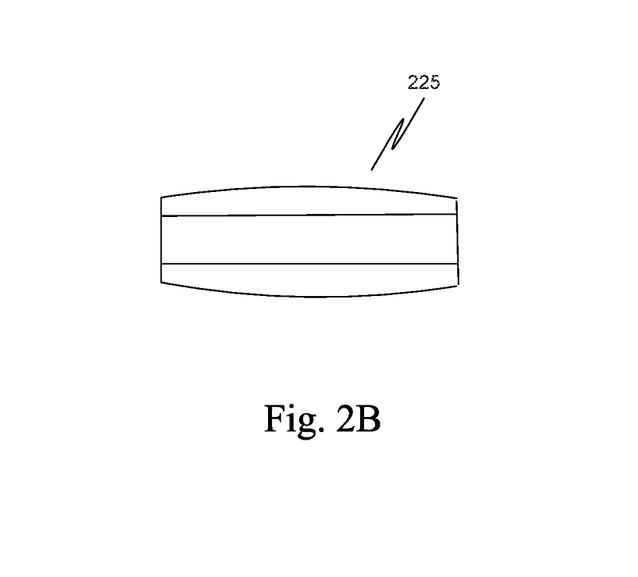
FIG. 2B is an illustration of one aspect of a lens in each of the lens assemblies of FIG. 2A.

Also captured in frame 300 are fixed reflections 391-1, 392-1, 393-1, 391-2, 392-2, and 393-2. In FIG. 3, the areas of the fixed reflections are stippled to make them easily distinguishable. If viewer optic spacing 240 remains fixed and the illumination source remains fixed in space, the locations of fixed reflections 391-1, 392-1, 393-1, 391-2, 392-2, and 393-2 do not change from captured frame to captured frame, because fixed reflections 391-1, 392-1, 393-1, 391-2, 392-2, and 393-2 are produced by the edges between the different components of viewing lens 225 (FIG. 2B).

The use of three fixed reflections from each viewing lens is illustrative only and is not intended to be limiting. The number of and size of the fixed reflections depends on the configuration and composition of the components making up viewing lens 225 and whether an anti-reflective coating is used between the components. Irrespective of the number of fixed reflections, the techniques described herein for minimizing the effect of the fixed reflections on eye-tracking are the same.

In addition to fixed reflections 391-1, 392-1, 393-1, 391-2, 392-2, and 393-2, a corneal reflection 396-1 from a cornea of the user's left eye 290-L and a corneal reflection 396-2 from a cornea of the user's right eye 290-R are also captured in frame 300. In FIG. 3, the areas of the corneal reflections also are stippled to make them easily distinguishable.

The locations of corneal reflections 396-1 and 396-2 change from captured frame to captured frame as the direction of the user's gaze changes. FIG. 3 illustrates a vector 397-1 between corneal reflection 396-1 and the center of the image of the pupil of the user's right eye and a vector 397-2 between corneal reflection 396-2 and the center of the image of the pupil of the user's right eye.

It is known to use a vector between the center of the pupil and the corneal reflection to determine the direction of a user's gaze. See, for example, U.S. Pat. No. 4,836,670 (issued Jun. 6, 1989, disclosing "Eye Movement Detector") and U.S. Pat. No. 4,950,069 (issued Aug. 21, 1990, disclosing "Eye Movement Detector With Improved Calibration and Speed), each of which is incorporated herein by reference. Also, it is noted that feature extraction from information in a captured frame is known to those knowledgeable in the field, and so is not considered in detail herein. In particular, techniques for detecting the pupil and/or iris in an image of an eye using feature extraction are known, and so are not considered in detail herein. Finally, it is also know how to determine the center of the pupil from the detected pupil and/or iris. Thus, the details of eye-tracking are not considered in further detail herein.

Fixed reflections are detected by comparing locations of reflections in frames captured by eye-tracking image capture unit 210. If the location of a reflection does not change from frame to frame, the reflection is considered a fixed reflection. As discussed more completely below, one aspect, a list of information characterizing the fixed reflections is used by controller 260 in determining whether a fixed reflection is likely to interfere with eye-tracking. This requires storing of the list.

In another aspect, a bitmap is used by controller 260 in determining whether a fixed reflection is likely to interfere with eye-tracking. Pixel locations in the bitmap corresponding to a fixed reflection in a captured frame are set to one state and all other locations in the bitmap are set to a different state. Since the locations of the fixed reflections do not change from frame to frame, comparison of the bitmaps for different frames can determine whether a glint has intersected a fixed reflection.

Prior to further considering changing the locations of the fixed reflections in a captured frame to facilitate eye-tracking, it is helpful to understand aspects of the configuration of the eye-tracking illuminator in relation to the eye-tracking image capture unit in stereoscopic image viewer 200. FIGS.

Figure 4A:
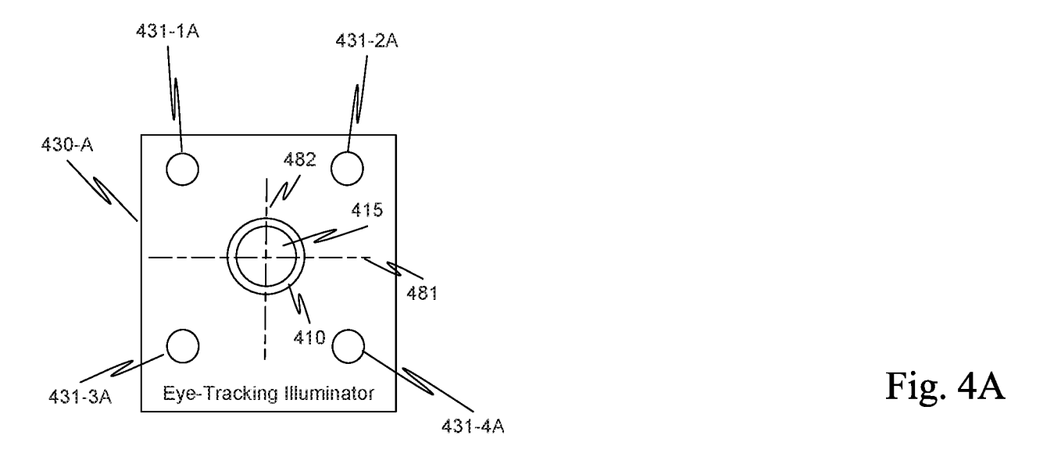
FIGS. 4A and 4B are illustrations of eye-tracking illuminator and an eye-tracking image capture unit suitable for use in the stereoscopic image viewer of FIG. 2.
Figure 4B:
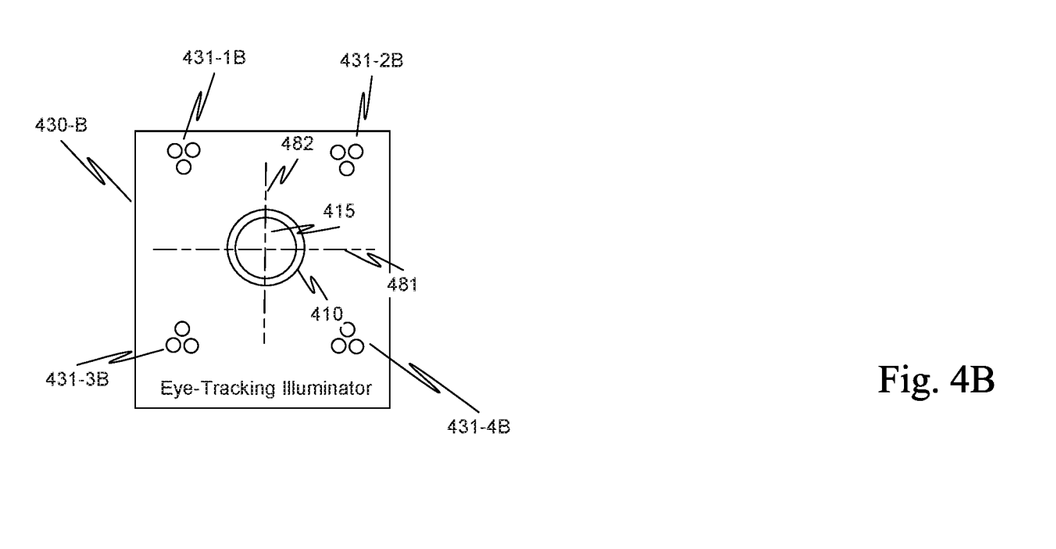

4A and 4B are illustrations of different aspects of a combination of an eye-tracking image capture unit and an eye-tracking illuminator that is included within stereoscopic image viewer 200.

Eye-tracking image capture unit 410 includes an eye-tracking image capture unit lens assembly 415 that is mounted on a board that includes electronics for capturing, processing, and passing a frame of image data to controller 260. The board also receives control information from controller 260.

In FIG. 4A, eye-tracking image capture unit 410 is coupled to a first eye-tracking illuminator 430-A. Eye-tracking illuminator 430A includes a plurality of non-visible light sources 431-1A, 431-2A, 431-3A, and 431-4A, e.g., infrared light sources. Plurality of non-visible light sources 431-1A, 431-2A, 431-3A, and 431-4A includes sets of non-visible light sources. In this example, each of plurality of non-visible light sources 431-1A, 431-2A, 431-3A, and 431-4A is a single light source, e.g., an infrared light emitting diode.

In this example, a first set of non-visible light sources 431-1A, 431-3A is to the left of a vertical axis 482 of eye-tracking image capture unit lens assembly 415, e.g., displaced in a first direction from vertical axis 482 of eye-tracking image capture unit lens assembly 415. In this example, a second set of non-visible light sources 431-2A, 431-4A is to the right of vertical axis 482 of eye-tracking image capture unit lens assembly 415, e.g., displaced in a second direction from eye-tracking image capture unit lens assembly 415. The second direction is in a direction opposite the first direction along horizontal axis 481, in this example. In one aspect, first set of non-visible light sources 431-1A, 431-3A and second set of non-visible light sources 431-2A, 431-4A are equally spaced from vertical axis 482.

For each set of non-visible light sources, the light sources in the set are equally spaced above and below horizontal axis 481 of eye-tracking lens assembly. Specifically, for first set of non-visible light sources 431-1A, 431-3A, nonvisible light source 431-1A is above horizontal axis 481 of eye-tracking image capture unit lens assembly 415, e.g., displaced in a third direction from horizontal axis 481 of eye-tracking image capture unit lens assembly 415. Non-visible light source 431-3A is below horizontal axis 481 of eye-tracking image capture unit lens assembly 415, e.g., displaced in a fourth direction from horizontal axis 481 of eye-tracking image capture unit lens assembly 415. The third direction is in a direction opposite the fourth direction along vertical axis 482, in this example. Non-visible light sources 431-1A and non-visible light source 431-3A are equally spaced from horizontal axis 481.

Similarly, for second set of non-visible light sources 431-2A, 431-4A, nonvisible light source 431-2A is above horizontal axis 481 of eye-tracking image capture unit lens assembly 415, e.g., displaced in a third direction from horizontal axis 481 of eye-tracking image capture unit lens assembly 415. Nonvisible light source 431-4A is below horizontal axis 481 of eye-tracking image capture unit lens assembly 415, e.g., displaced in a fourth direction from horizontal axis 481 of eye-tracking image capture unit lens assembly 415. Again, the third direction is in a direction opposite the fourth direction along vertical axis 482, in this example. Non-visible light sources 31-2A and non-visible light source 431-4A are equally spaced from horizontal axis 481.

First set of non-visible light sources 431-1A, 431-3A is used to illuminate left eye 290-L of a user, while second set of non-visible light sources 431-2A, 431-4A is used to illuminate right eye 290-R of the user. At any point in time if non-visible light is used to illuminate the eye of the user, only one non-visible light source in a set of non-visible light sources is used to illuminate the eye of the user. Each non-visible light source has two states—one in which non-visible light is output, and one in which non-visible light is not output. Controller 260, in this example, individually controls the state of each of plurality of non-visible light sources 431-1A, 431-2A, 431-3A, and 431-4A.

In FIG. 4B, eye-tracking image capture unit 410 is coupled to a second eye-tracking illuminator 430-B. Eye-tracking illuminator 430-B includes a first plurality of non-visible light sources 431-1B, 431-2B, 431-3B, and 431-4B, e.g., infrared light sources. In this example, each of first plurality of non-visible light sources 431-1B, 431-2B, 431-3B, and 431-4B includes a different second plurality of single light sources, e.g., a plurality of infrared light emitting diode. In this example, each of the second plurality of single light sources is three light sources. The second plurality of single light sources can be useful in identifying a fixed reflection.

While each of plurality of non-visible light sources 431-1B, 431-2B, 431-3B, and 431-4B includes more than one light source, plurality of non-visible light sources 431-1B, 431-2B, 431-3B, and 431-4B are grouped into sets of non-visible light sources as described for FIG. 4A, and are arranged about eye-tracking image capture unit lens assembly 415 in a way that is equivalent to that described with respect to FIG. 4A, and so that description is not repeated here for second eye-tracking illuminator 430-B. In this example, each light source in a set is made up of a plurality of single light sources.

Figure 5A:
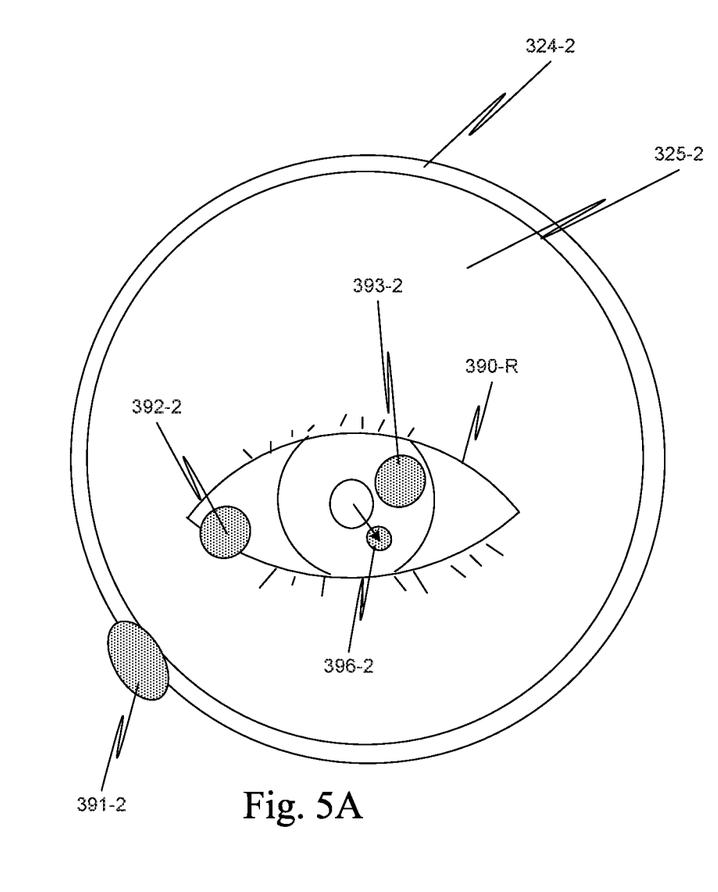
FIGS. 5A to 5C illustrate controller management of fixed reflections using an eye-tracking illuminator.
Figure 5B:
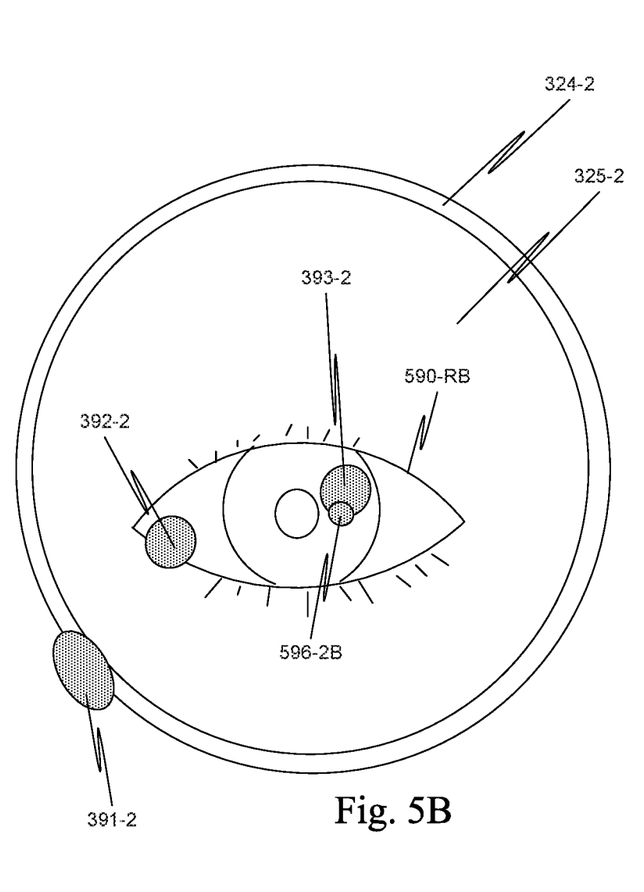
Figure 5C:
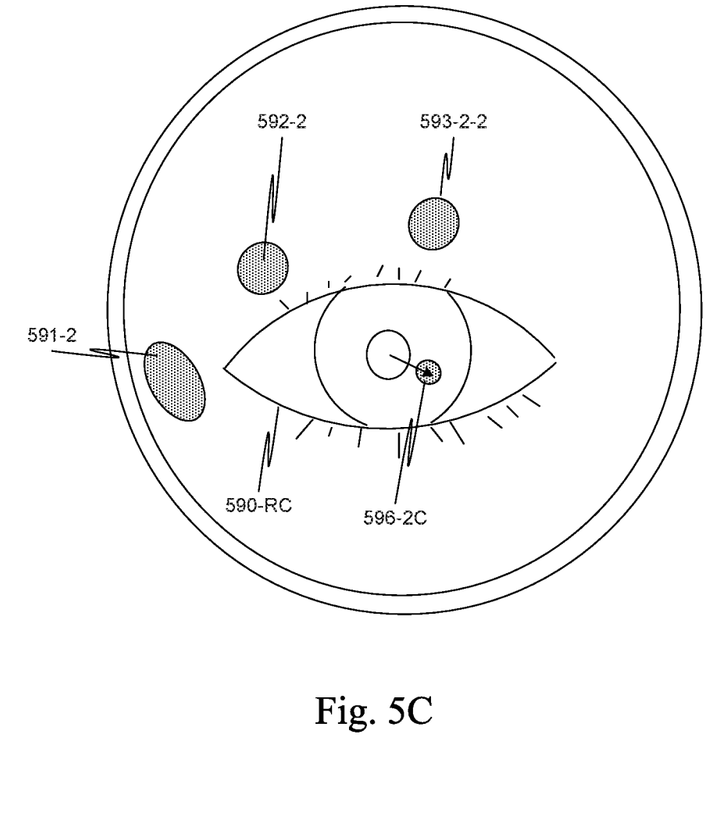

FIGS. 5A to 5C illustrate management of fixed reflections caused by viewing lens 225 by controller 260 using an eye-tracking illuminator. In this example, only the images associated with fixed reflections and a gaze of a user's right eye are considered. The considerations of the images associated with fixed reflections and a gaze of a user's left eye are equivalent to the following description, and so are not repeated.

Each of FIGS. 5A to 5C is an illustration of an image that includes an image 324-2 of a lens retainer ring and an image 325-2 of a lens, an image of a user's eye, fixed reflections, and a corneal reflection. In FIG. 5A, three fixed reflections 391-2, 392-2 and 393-2 are shown. Corneal reflection 396-2 is closest to fixed reflection 393-2, but does not intersect fixed reflection 393-2.

In one aspect, if any part of corneal reflection 396-2 intersects a fixed reflection, the accuracy of determining the user's gaze is considered unacceptable, and the illumination is changed. In another aspect, only if corneal reflection 396-2 completely intersects with, e.g., merges with, a fixed reflection is the illumination changed.

In FIG. 5A, corneal reflection 396-2 does not intersect with any of fixed reflections 391-2, 392-2 and 393-2. Thus, controller 260 does not change the illumination source used to illuminate the user's right eye.

In one aspect, the information characterizing corneal reflection 396-2 is compared with stored information for each of the fixed reflections to determine whether there is an intersection. In another aspect, as described below, a bitmap is used in determining whether there is an intersection.

In FIG. 5B, the captured frame that includes image 590-RB of the user's right eye show that the direction of the user's gaze has changed. Corneal reflection 596-2B intersects fixed reflection 393-2. Consequently, controller 260 stops the light output from the light source illuminating the user's right eye and enables a different light source to output light, e.g., controller 260 switches the light source that is outputting light, which changes the location of the light source, and consequently changes the location of fixed reflections in subsequently captured frames. In some aspects, a bounding geometric element, e.g., a rectangle, an ellipse, etc., is defined around the glint, and it is the intersection of the bounding geometric element with a bounding geometric element for the fixed reflection that is detected. Alternatively, the intersection of a boundary of the glint and a boundary of the fixed reflection can be detected.

Using eye-tracking illuminator 430-A as an example, light source 431-4A of second set of non-visible light sources 431-2A, 431-4A provided the illumination for the capture of the frames including the images of FIGS. 5A and 5B. Thus, controller 260 stops light output from non-visible light source 431-4A and enables non-visible light source 431-2A to output light. Since the location of the light source changed, the locations of the fixed reflections in subsequently captured frames change.

In particular, as illustrated in FIG. 5C, for a captured frame that includes image 596-RC of the user's right eye, fixed reflections 591-2, 592-2, 593-2 have changed location in comparison to the corresponding fixed reflections 391-2, 392-2, 393-2 in FIG. 5B. Consequently, corneal reflection 596-2C no longer intersects any fixed reflection. Thus, by changing the light source used to illuminate the user's right eye, controller 260 prevented the fixed reflections from interfering with tracking the user's gaze.

In one aspect, a list of fixed reflections is generated for each of the light sources in the plurality of non-visible light sources. The information in the list of fixed reflections is used in determining whether a corneal reflection intersects a fixed reflection, and consequently, the list of fixed reflections is used to determine when to change the location of the light source used to illuminate a user's eye.

The lists of information characterizing fixed reflections are stored, either in controller 260, in cloud storage, or in stereoscope image viewer 200, for subsequent use during eye-tracking. The list of information characterizing fixed reflections remains valid so long as viewer optic spacing 240 does not change.

In one aspect, for each captured frame, controller 260 creates a bitmap. The bitmap includes a bit for each pixel in a captured frame. Initially, all the bits in the bitmap are set to a first state, e.g., zero. When a reflection, either a fixed reflection or a glint, is detected in the captured frame, the locations in the bitmap corresponding to the locations of the fixed reflection and the glint in the captured frame are set to a second state, e.g., one.

Figure 6:
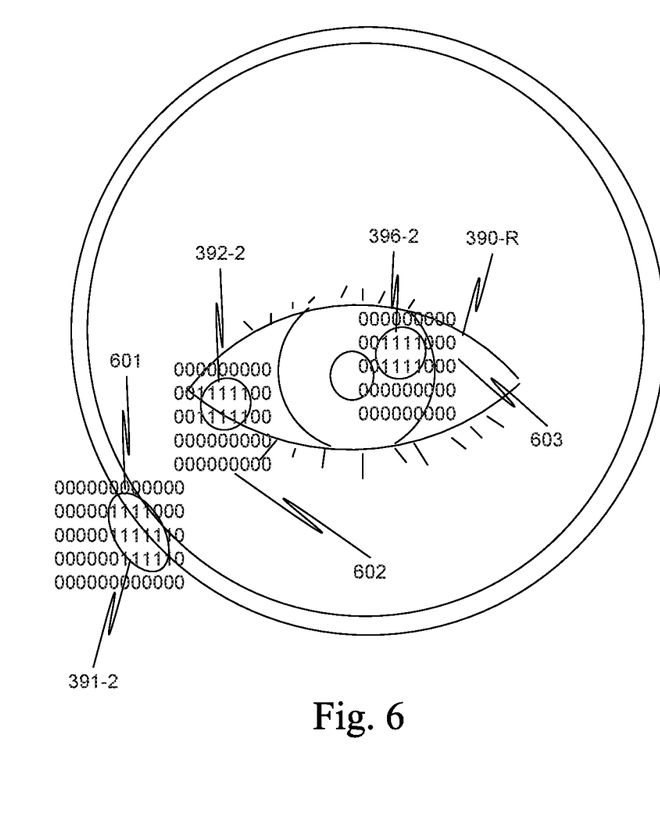
FIG. 6 illustrates fixed reflections overlain with portions of a bitmap that represents the fixed reflections.

FIG. 6 illustrates fixed reflections 391-2, 392-2, and 393-2 overlain with portions 601, 602, and 603 of a bitmap that represents the fixed reflections. Note that for pixels within a fixed reflection, the bits have a value of one, and all other bits have a value of zero. This bitmap is associated with light source 431-4A in FIG. 4A.

In one aspect, use of a bitmap to identify the regions of fixed reflections eliminates the need to store a list. Initially, for each frame, a bitmap starts with all bits set to zero—a first state—and bits in the bitmaps associated with reflected light—fixed reflections and possibly a glint—are set to one—a second state. Then, for each frame, the bitmap for that frame is subtracted from a bitmap for a frame captured previously to obtain a new bitmap.

If all the bits in the new bitmap have the first state, i.e., all the bits have the same state, controller 260 switches the light source illuminating the user's eye, because the glint has merged with one of the fixed reflections. If the bits in the new bitmap have different states, i.e., some bits have the first state and other bits have the second state, controller 260 does not change the light source illuminating the user's eye, because the glint has not merged with one of the fixed reflections.

When two bitmaps are subtracted and all the bits in the new bitmap have the same state, it means that the reflections are not changing from frame to frame, and so the glint has intersected one of the fixed reflections. When two bitmaps are subtracted, if there is a glint that has not merged with a fixed reflection, the subtraction of the two bitmaps results in a new bit map with some bits having the second state and some bits having the first state, i.e., the bits in the new bitmap have different states. In one aspect, at least two consecutive new bitmaps with bits all having the same state are required, before controller 260 switches the location of the illumination source.

In some situations, a glint may have intersected a fixed reflection, but the glint has not merged with the fixed reflection. In this case, when two bitmaps are subtracted, the new bitmap has a bit or bits with a different state from all the other bits, e.g., there are some bits that have a state of one. (Here, a new bitmap is that bitmap that results from subtraction of a bitmap for a second frame from a bitmap for a first frame.)

The bits with a state of one in the new bitmap represent a possible glint. To ascertain whether the bits with a state of one in the new bitmap represent a glint, the number of adjacent bits having a state of one is compared with a glint threshold. If the number of adjacent bits in the new bitmap having a state of one is greater than the glint threshold, the region associated with the bits is considered a glint, and the location of the illumination source is not changed. If the number of adjacent bits having a state of one is less than the glint threshold, the region associated with the bits is not considered a glint, and the frame is not used in eye-tracking. If two consecutive new bitmaps have regions with a state of one, but the regions are not considered a glint, the location of the illumination source is changed, because this situation indicates that the glint has intersected a fixed reflection.

In one aspect, the glint threshold is empirically determined. The smallest glint detectable, i.e., the glint threshold, is empirically determined by the physical geometry of stereoscopic image viewer 200, the viewing lenses, and the resolution/field of view of eye-tracking image capture unit 210. In one aspect, the glint threshold is in a range of three to five pixels in diameter.

Figure 7:
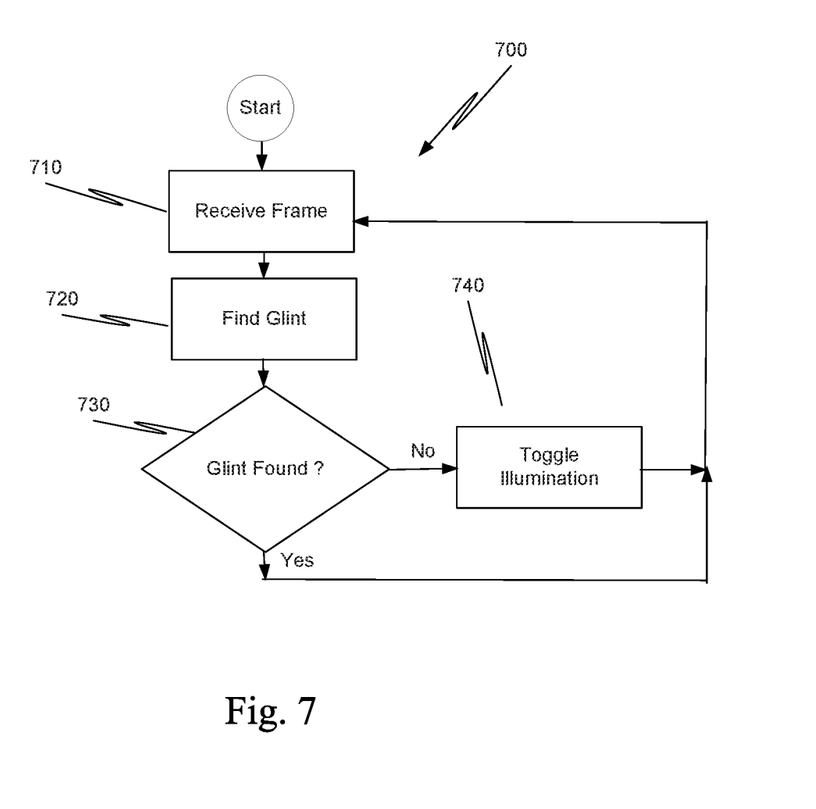
FIG. 7 is a high level process flow diagram for a method used by the controller of FIG. 2A.

FIG. 7 is a high level process flow diagram for a method 700 used by controller 260 to move the fixed reflections out of the way of eye-tracking. In RECEIVE FRAME act 710, a frame captured by eye-tracking image capture unit 210 is received. Upon receipt of the captured frame, processing transfers from RECEIVE FRAME act 710 to FIND GLINT act 720.

FIND GLINT act 720 determines whether glints were found in the captured frame—one for each of the user's eyes. This can be done by either using stored information on the fixed reflections or by using bitmaps, as described above. Upon completion of FIND GLINT act 720, processing transfers from FIND GLINT act 720 to GLINT FOUND check process 730.

In GLINT FOUND check process 730, if a glint was not found, processing transfers to TOGGLE ILLUMINATION act 740. If a glint was found, processing returns to RECEIVE FRAME act 710.

In TOGGLE ILLUMINATION act 740, controller 260 changes the non-visible light source that illuminates the user's eye, e.g., moves the fixed reflection such that the fixed reflection is not in a location that may interfere with eye-tracking. Upon completion, TOGGLE ILLUMINATION act 740 transfers to RECEIVE FRAME act 710

In the aspects described above, a fixed reflection was large enough that if a corneal reflection merged with the fixed reflection, the accuracy of the eye-tracking was compromised, and so the fixed reflection was moved out of the way. In another aspect, if the corneal reflection of one of the user's two eyes merges with a fixed reflection, but the other does not, the gaze vector associated with the corneal reflection that is not affected by the fixed reflection is used in determining the direction of the user's gaze instead of both of the gaze vectors. This may result in a somewhat reduced accuracy in determining the user's gaze, but the reduced accuracy is still sufficient to reliably determine the gaze direction so that it is not necessary to move the fixed reflection out of the way by changing the location of the light source.

In yet another aspect, if a fixed reflection has a region that is the same as or smaller than the region associated with the corneal reflection, the merger of the two reflections will result in a combined reflection region that ranges from less than twice the region of the corneal refection to the size of the corneal reflection. In this case, the use of the combined reflection region in determining the user's gaze provides sufficient accuracy so that it is not necessary to move the fixed reflection out of the way by changing the location of the light source.

As used herein, "first," "second," "third," "fourth," etc. are adjectives used to distinguish between different components or elements. Thus, "first," "second," "third," "fourth," etc. are not intended to imply any ordering of the components or elements.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

As explained above, the controller described herein can be implemented by software executing on a processor, hardware, firmware, or any combination of the three. When the controller is implemented as software executing on a processor, the software is stored in a memory as computer readable instructions and the computer readable instructions are executed on the processor. All or part of the memory can be in a different physical location than a processor so long as the processor can be coupled to the memory. Memory refers to a volatile memory, a non-volatile memory, or any combination of the two.

Also, the functions of the controller, as described herein, may be performed by one unit, or divided up among different components, each of which may be implemented in turn by any combination of hardware, software that is executed on a processor, and firmware. When divided up among different components, the components may be centralized in one location or distributed across the system for distributed processing purposes. The execution of the controller results in methods that perform the processes described above for the controller.

A processor is coupled to a memory containing instructions executed by the processor. This could be accomplished within a computer system, or alternatively via a connection to another computer via modems and analog lines, or digital interfaces and a digital carrier line, or via connections using any of the protocols described above. In view of this disclosure, instructions used in any part of or all of the processes described herein can be implemented in a wide variety of computer system configurations using an operating system and computer programming language of interest to the user.

Herein, a computer program product comprises a computer readable medium configured to store computer readable code needed for any part of or all of the processes described herein, or in which computer readable code for any part of or all of those processes is stored. Some examples of computer program products are CD-ROM discs, DVD discs, flash memory, ROM cards, floppy discs, magnetic tapes, computer hard drives, servers on a network and signals transmitted over a network representing computer readable program code. A non-transitory tangible computer program product comprises a tangible computer readable medium configured to store computer readable instructions for any part of or all of the processes or in which computer readable instructions for any part of or all of the processes is stored. Non-transitory tangible computer program products are CD-ROM discs, DVD discs, flash memory, ROM cards, floppy discs, magnetic tapes, computer hard drives, and other physical storage mediums.

All examples and illustrative references are non-limiting and should not be used to limit the claims to specific implementations and embodiments described herein and their equivalents. Any headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

We claim:

1. An apparatus comprising:
    a viewing lens;
    a display device configured to output a visible light image for viewing by a user through the viewing lens;
    a plurality of light sources configured to output light used in tracking a gaze of the user while the user is viewing the visible light image through the viewing lens;
    an image capture unit;
    a reflective structure configured to
        reflect the visible light image output by the display device through the viewing lens, and
        pass a corneal reflection from the user to the image capture unit; and
    a controller configured to:
        generate the corneal reflection using a first one of the plurality of light sources; and
        switch to a second one of the plurality of light sources to generate the corneal reflection if the corneal reflection generated by the first one of the plurality of light sources intersects a fixed reflection that is from the viewing lens and that is captured by the image capture unit,
    wherein at least one light source included in the plurality of light sources is provided on a user side of the viewing lens and is configured to illuminate an eye of the user.

2. The apparatus of claim 1, wherein the viewing lens comprises: an outer surface; and an anti-reflective coating for the light from the plurality of light sources, the anti-reflective coating being on the outer surface of the viewing lens.

3. The apparatus of claim 1, wherein the plurality of light sources comprises a plurality of non-visible light sources.

4. The apparatus of claim 1:
    wherein the image capture unit comprises a lens assembly; and
    wherein the first one of the plurality of light sources is displaced in a first direction from the lens assembly of the image capture unit; and the second one of the plurality of light sources is displaced in a second direction from the lens assembly of the image capture unit, where the first direction is opposite to the second direction.

5. The apparatus of claim 1, further comprising a movable viewing assembly comprising the viewing lens and the reflective structure, the reflective structure passing a portion of the light from the plurality of light sources.

6. The apparatus of claim 5, wherein:
    the viewing lens is fixedly coupled to the reflective structure in the movable viewing assembly; and
    the viewing lens and the reflective structure move as a unit as the movable viewing assembly moves.

7. The apparatus of claim 6, wherein:
    the movable viewing assembly further comprises the display device mounted in the movable viewing assembly to provide the visible light image to the reflective structure;
    the display device is fixedly coupled to the reflective structure in the movable viewing assembly; and
    the viewing lens, the reflective structure, and the display device move as a unit as the movable viewing assembly moves.

8. The apparatus of claim 1, wherein the reflective structure comprises a dichroic surface.

* * * * *